United States Patent
Yu et al.

(10) Patent No.: US 7,635,703 B2
(45) Date of Patent: Dec. 22, 2009

(54) IMIDAZOLE SUBSTITUTED PYRAZOLE KINASE INHIBITORS

(75) Inventors: Yang Yu, Brookfield, CT (US); Ronghui Lin, East Brunswick, NJ (US); Peter J. Connolly, New Providence, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 91 days.

(21) Appl. No.: 11/871,463

(22) Filed: Oct. 12, 2007

(65) Prior Publication Data

US 2008/0103172 A1  May 1, 2008

Related U.S. Application Data

(60) Provisional application No. 60/829,745, filed on Oct. 17, 2006.

(51) Int. Cl.
- A61K 31/4725 (2006.01)
- A61K 31/4439 (2006.01)
- C07D 401/14 (2006.01)
- A61P 25/28 (2006.01)
- A61P 3/10 (2006.01)
- C07D 217/02 (2006.01)

(52) U.S. Cl. .................... 514/307; 514/341; 546/272.2; 546/148

(58) Field of Classification Search ............... 546/272.7, 546/148; 514/341, 307
See application file for complete search history.

(56) References Cited

U.S. PATENT DOCUMENTS 4,999,269 A * 3/1991 Emoto et al. ............... 430/59.3

OTHER PUBLICATIONS

Caligiuri et al., Chemistry & biology, (Oct. 2005) vol. 12, No. 10, pp. 1103-1115.*
Lin et al., Design, Synthesis, and Evaluation of 3,4-Disubstituted Pyrazole Analogues as Anti-Tumor CDK Inhibitors, Bioorganic & Medicinal Chemistry Letters (2007), vol. 17, pp. 4557-4561.
International Search Report dated Aug. 7, 2008 for International Appln. No. PCT/US2007/21848.

* cited by examiner

*Primary Examiner*—D. Margaret Seaman
*Assistant Examiner*—Niloofar Rahmani
(74) *Attorney, Agent, or Firm*—Andrea Jo Kamage

(57) ABSTRACT

The present invention is directed to novel substituted pyrazole compounds of Formula (I) or a form or composition thereof

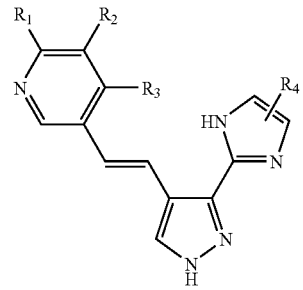

and the use thereof as inhibitors of ATP-protein kinase interactions.

6 Claims, No Drawings

IMIDAZOLE SUBSTITUTED PYRAZOLE KINASE INHIBITORS

CROSS REFERENCE TO RELATED APPLICATIONS

This application claims priority of the filing date of U.S. Provisional application Ser. No. 60/829,745 filed Oct. 17, 2006, entitled "Imidazole substituted pyrazole kinase inhibitors," the entire disclosures of which are hereby incorporated by reference into the present disclosure.

FIELD OF THE INVENTION

The present invention is in the area of novel substituted pyrazole compounds or forms thereof, their synthesis and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Protein kinases catalyze and regulate the process of phosphorylation. Phosphorylation modulates or regulates a variety of cellular processes such as proliferation, growth, differentiation, metabolism, apoptosis, motility, transcription, translation and other signaling processes. Uncontrolled signaling for cell growth due to defective control of protein phosphorylation has also been implicated in a number of diseases.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases. Therefore, kinase inhibitors have potential use as therapeutic agents.

There is a need for potent small-molecule kinase inhibitors of one or more of the CDK1, HER2, VEGFR2, or Aurora-A kinase proteins and the like possessing anti-tumor cell proliferation activity, and as such are useful for treating a CDK1, HER2, VEGFR2, or Aurora-A kinase receptor mediated, angiogenesis-mediated or hyperproliferative disorders.

PCT patent application WO97/28158 describes imidazoles as endothelin receptor antagonists.

SUMMARY OF THE INVENTION

A first aspect of the present invention is novel compounds of Formula (I) or a form thereof:

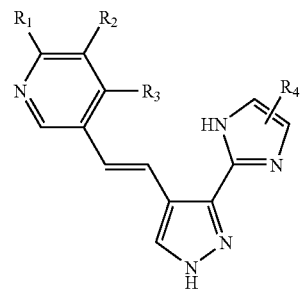

as inhibitors of ATP-protein kinase interactions, wherein $R_1$, $R_2$, $R_3$ and $R_4$ are as defined herein.

A sec aspect of this invention is a composition or medicament comprising one or more compounds of Formula (I) or a form thereof.

A third aspect of this invention is a method of synthesizing compounds of Formula (I) or a form thereof.

A fourth aspect of this invention is the use of one or more compounds of Formula (I) or a form thereof as protein kinase inhibitors. The aspect of the protein kinases includes serine/threonine kinases and tyrosine kinases. The aspect of the kinases further includes kinase selected from CDK1, HER2, VEGFR2, or Aurora-A. Also in this aspect, the compounds of Formula (I) or a form thereof are useful for preventing, treating or ameliorating chronic or acute kinase mediated diseases.

A fifth aspect of this invention is a method for ameliorating, treating or preventing a chronic or acute kinase mediated disease in a patient in need thereof comprising administering to the patient an effective amount of one or more compounds of Formula (I) or a form thereof.

In this aspect, the chronic or acute disease is mediated by a kinase selected from CDK1, HER2, VEGFR2, or Aurora-A. Also in this aspect, the method includes inhibiting unregulated kinase activity in the patient. The aspect of unregulated kinase activity includes unregulated kinase expression or signaling, unregulated expression or signaling of a kinase selected from CDK1, HER2, VEGFR2, or Aurora-A and unregulated expression or signaling which results in unregulated cell proliferation. The aspect of unregulated cell proliferation includes cancer, metastatic cancer cell invasion or metastatic cancer cell migration. The aspect of cancer includes tumors mediated by the unregulated activity of kinases selected from CDK1, HER2, VEGFR2, or Aurora-A. The aspect of cancer further includes non-small-cell lung cancers, colon cancers, breast cancers and the like. An aspect of the method includes an amount of one or more compounds of Formula (I) or a form thereof which is effective to induce remission of a chronic form of a cancer. The aspect of the effective amount includes an amount, which is effective at a low dose to inhibit unregulated kinase activity.

A sixth aspect of this invention is a method for use of one or more compounds of Formula (I) or a form thereof in the preparation of a composition or medicament for preventing, treating or ameliorating chronic or acute kinase mediated diseases in a patient in need thereof. This aspect of the method includes administering to the patient an effective amount of a compound of Formula (I) or a form thereof in the form of a composition or medicament.

These and other aspects and advantages of the invention, which will become apparent in light of the detailed description below, are achieved through use of the compounds of this invention.

DETAILED DESCRIPTION OF THE INVENTION

The present invention provides pyrazole compounds of Formula (I):

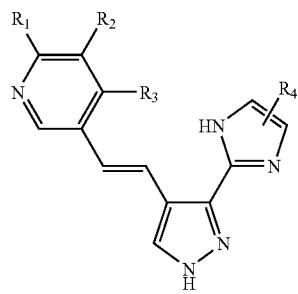

and a form thereof, wherein $R_1$ is hydrogen, hydroxy, halo, $C_{1-6}$alkyl, $C_{1-6}$alkoxy, amino or $C_{1-6}$alkyl-amino;

$R_2$ is hydrogen, hydroxy, $C_{1-6}$alkyl, $C_{1-6}$alkoxy, amino, $C_{1-6}$alkyl-amino, amino-$C_{1-6}$alkyl, $C_{1-6}$alkyl-amino-$C_{1-6}$alkyl, $C_{1-6}$alkoxy-carbonyl, $C_{1-6}$alkyl-amino-carbonyl or cyano;

$R_3$ is hydrogen or $C_{1-6}$alkyl;

alternatively, $R_2$ and $R_3$ are taken together to form —CH=CH—CH=CH—; and $R_4$ is hydrogen, trihalo-$C_{1-6}$alkyl, trihalo-$C_{1-6}$alkoxy or cyano.

An example of the present invention is a compound of Formula (I) and a form thereof wherein $R_1$ is hydrogen, halo or amino.

An example of the present invention is a compound of Formula (I) and a form thereof wherein $R_2$ is hydrogen, $C_{1-6}$alkoxy, $C_{1-6}$alkyl-amino-$C_{1-6}$alkyl, $C_{1-6}$alkoxy-carbonyl, $C_{1-6}$alkyl-amino-carbonyl or cyano.

An example of the present invention is a compound of Formula (I) and a form thereof wherein $R_3$ is hydrogen.

An example of the present invention is a compound of Formula (I) and a form thereof wherein $R_3$ is $C_{1-6}$alkyl.

An example of the present invention is a compound of Formula (I) and a form thereof wherein $R_2$ and $R_3$ are taken together to form —CH=CH—CH=CH—.

An example of the present invention is a compound of Formula (I) and a form thereof wherein $R_4$ is hydrogen, trihalo-$C_{1-6}$alkyl or cyano.

An example of the present invention is a compound of Formula (I) and a form thereof wherein $R_4$ is hydrogen, trifluoro-$C_{1-6}$alkyl or cyano.

An example of the present invention is a compound of Formula (I) and a form thereof wherein $R_4$ is hydrogen, trifluoro-methyl or cyano.

Compounds representative of a compound of Formula (I) or a form thereof include compounds and forms thereof selected from:

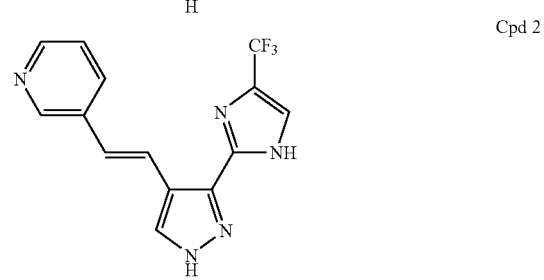

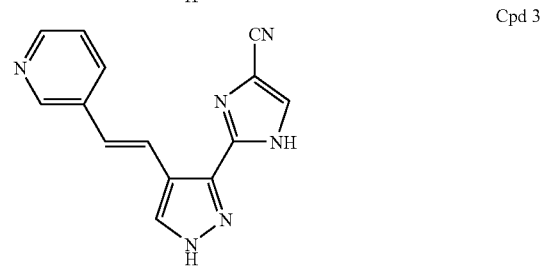

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means a stereoisomer that is not nonsuperimposable with its mirror image. The term "diastereomer" means stereoisomers that are not enantiomers.

The term "chiral molecule" means a molecule that has at least one pair of enantiomers. This is in contrast to achiral molecules, which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Chemical Definitions

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-6}$alkyl," whether used alone or as part of a substituent group, means a straight or branched chain monovalent hydrocarbon alkyl radical or alkyldiyl linking group, respectively, comprising from 1 to 6 carbon atoms, wherein the radical is derived by the removal of one hydrogen atom from a single carbon atom and the alkyldiyl linking group is derived by the removal of one hydrogen atom from each of two carbon atoms in the chain, such as, for example methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl and the like. Examples include $C_{1-4}$alkyl groups. $C_{1-6}$alkyl is substituted on one or more available carbon chain atoms with one or more substituents when allowed by available valences.

The term "$C_{1-6}$alkoxy" means an alkyl radical or linking group having from 1-6 carbon atoms in a linear or branched arrangement, wherein the radical or linking group is attached through an oxygen linking atom, as in the formula: —O—$C_{1-6}$alkyl. The term "$C_{1-6}$alkoxy" also includes a "$C_{1-4}$ alkoxy" radical or linking group having from 1 up to 4 carbon atoms respectively, such as methoxy, ethoxy, propoxy, butoxy and the like. An alkoxy radical or linking group may be attached to a core molecule and further substituted as a linking group where indicated.

The term "$C_{1-6}$alkoxy-carbonyl" means a radical of the formula: —C(O)—O—$C_{1-6}$alkyl, wherein $C_{1-6}$alkyl is optionally further substituted.

The term "$C_{1-6}$alkyl-amino" means a radical of the formula: —NH—$C_{1-6}$alkyl or —N($C_{1-6}$alkyl)$_2$, wherein $C_{1-6}$alkyl is optionally further substituted.

The term "$C_{1-6}$alkyl-amino-$C_{1-6}$alkyl" means a radical of the formula: —$C_{1-6}$alkyl-NH—$C_{1-6}$alkyl or —$C_{1-6}$alkyl-N($C_{1-6}$alkyl)$_2$, wherein $C_{1-6}$alkyl is optionally further substituted.

The term "$C_{1-6}$alkyl-amino-carbonyl" means a radical of the formula: —C(O)—NH—$C_{1-6}$alkyl or —C(O)—N($C_{1-6}$alkyl)$_2$, wherein $C_{1-6}$alkyl is optionally further substituted.

The term "amino" means a radical of the formula: —NH$_2$.

The term "amino-$C_{1-6}$alkyl" means a radical of the formula: —$C_{1-6}$alkyl-NH$_2$.

The term "halogen" or "halo" means the group chloro, bromo, fluoro or iodo.

The term "trihalo-$C_{1-6}$alkoxy" means a radical of the formula: —O—$C_{1-6}$alkyl-(halo)$_3$, wherein three halogen atoms may be substituted on $C_{1-6}$alkyl when allowed by available valences and includes trifluoromethoxy, trifluoroethoxy and the like.

The term "trihalo-$C_{1-6}$alkyl" means a radical of the formula: —$C_{1-6}$alkyl-(halo)$_3$, wherein three halogen atoms may be substituted on $C_{1-6}$alkyl when allowed by available valences and includes trifluoromethyl, trifluoroethyl and the like.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Use

A first aspect of the present invention is compounds of Formula (I) or a form thereof useful as inhibitors of ATP-protein kinase interactions.

A second aspect of this invention is a composition or medicament comprising one or more compounds of Formula (I) or a form thereof.

A third aspect of this invention is the use of one or more compounds of Formula (I) or a form thereof as protein kinase inhibitors. The aspect of the protein kinases includes serine/threonine kinases and tyrosine kinases. The aspect of the kinases further includes kinase selected from CDK1, HER2, VEGFR2, or Aurora-A. Also in this aspect, the compounds of Formula (I) or a form thereof are useful for preventing, treating or ameliorating chronic or acute kinase mediated diseases. The aspect of a kinase mediated disease includes an EGFR protein kinase mediated cytomegalovirus infection. In a related aspect, the compounds of Formula (I) or a form thereof are useful contraceptive agents.

The use of one or more compounds of Formula (I) or a form thereof as protein kinase inhibitors thus includes use of one or more compounds of Formula (I) or a form thereof for inhibiting unregulated protein kinase activity by contacting a protein kinase or protein kinase receptor with one or more compounds of Formula (I) or a form thereof. Accordingly, inhibiting such unregulated activity includes inhibiting unregulated expression or signaling and, thus, includes use of one or more compounds of Formula (I) or a form thereof for inhibiting unregulated cell proliferation.

A fourth aspect of this invention is a method for ameliorating, treating or preventing a chronic or acute kinase mediated disease in a patient in need thereof comprising administering to the patient an effective amount of one or more compounds of Formula (I) or a form thereof.

In this aspect, the chronic or acute disease is mediated by a kinase selected from CDK1, HER2, VEGFR2, or Aurora-A. Also in this aspect, the method includes inhibiting unregulated kinase activity in the patient. The aspect of unregulated kinase activity includes unregulated kinase expression or signaling, unregulated expression or signaling of a kinase selected from CDK1, HER2, VEGFR2, or Aurora-A and unregulated expression or signaling which results in unregulated cell proliferation. The aspect of unregulated cell proliferation includes cancer, metastatic cancer cell invasion or metastatic cancer cell migration. The aspect of cancer includes tumors mediated by the unregulated activity of kinases selected from CDK1, HER2, VEGFR2, or Aurora-A. The aspect of cancer further includes non-small-cell lung cancers, colon cancers, breast cancers and the like. An aspect of the method includes an amount of one or more compounds of Formula (I) or a form thereof which is effective to induce remission of a chronic form of a cancer. The aspect of the effective amount includes an amount that is effective at a low dose to inhibit unregulated kinase activity.

A fifth aspect of this invention is a method for use of one or more compounds of Formula (I) or a form thereof in the preparation of a composition or medicament for preventing, treating or ameliorating chronic or acute kinase mediated diseases in a patient in need thereof. This aspect of the method includes administering to the patient an effective amount of a compound of Formula (I) or a form thereof in the form of a composition or medicament.

The term "chronic or acute kinase mediated disease" as used herein, includes, and is not limited to diseases, disorders, syndromes or conditions associated with unregulated kinase activity and diseases, disorders, syndromes or conditions that accompany such activity.

The term "unregulated kinase activity" refers to 1) increased or unregulated kinase expression or signaling, 2) increased kinase expression leading to unregulated cell proliferation, 3) increased kinase signaling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that the compounds of Formula (I) or a form thereof are useful for treating, preventing or ameliorating chronic or acute kinase mediated diseases such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases.

The foregoing methods contemplate that a compound of formula (I) or a form thereof is useful for treating diseases, disorders or conditions such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases.

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; ocular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The term "administering" with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

Such methods include administering an effective amount of one or more compounds of Formula (I) or a form, composition or medicament thereof at different times during the course of a therapy or concurrently in a combination form.

Such methods further include administering an effective amount of one or more compounds of Formula (I) or a form, composition or medicament thereof with one or more agents at different times during the course of a therapy or concurrently in a combination form.

The term "prodrug" refers to a metabolic precursor of a compound of Formula (I) or a form thereof. In general, a prodrug is a functional derivative of a compound, which may be inactive when administered to a patient, but is readily convertible in vivo into an active metabolite compound.

The term "active metabolite" refers to a metabolic product of a compound that is effective for preventing, treating or ameliorating a chronic or acute kinase mediated disease. Conventional procedures for the selection and preparation of suitable prodrug derivatives are described, for example, in "Design of Prodrugs", ed. H. Bundgaard, Elsevier, 1985.

The term "patient" as used herein, refers to an animal, preferably a mammal, and most preferably a human, who has been the object of treatment, observation or experiment and is at risk of (or susceptible to) developing a disease or having a disease related to unregulated kinase activity.

The term "effective amount" refers to that amount of active compound or pharmaceutical agent that elicits the biological or medicinal response (such as inhibiting unregulated kinase activity) in a patient's tissue system, animal or human, that is being sought by a researcher, veterinarian, medical doctor, or other clinician, which includes preventing, treating or ameliorating the symptoms of the chronic or acute kinase mediated disease being treated.

The effective amount of a compound of Formula (I) exemplified in such a method is from about 0.001 mg/kg/day to about 300 mg/kg/day.

The term "composition" refers to a product containing one or more compounds of Formula (I) or a form thereof (such as a product comprising the specified ingredients in the specified amounts, as well as any product which results, directly or indirectly, from such combinations of the specified ingredients in the specified amounts).

The term "medicament" refers to one or more compounds of Formula (I) or a form thereof used in a product for use in preventing, treating or ameliorating a chronic or acute kinase mediated disease.

A formulation of a composition or medicament of the present invention is "pharmaceutically acceptable" when the molecular entities and components used therein are of sufficient purity and quality such that, when appropriately administered to an animal or a human, the formulation does not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination therapy" refers to the use of one or more compounds of Formula (I) or a form, composition or medicament thereof in combination with one or more therapeutic agents for preventing, treating or ameliorating a chronic or acute kinase mediated disease and advantageously may facilitate the use of a reduced effective dose of the compound of Formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The term "preventing, treating or ameliorating" refers, without limitation, to facilitating the eradication of, inhibiting the progression of or promoting stasis of a malignancy.

The term "radiation therapy" refers to a therapy that comprises exposing the patient in need thereof to radiation. The present invention includes a method for administering one or more compounds of Formula (I) or a form, composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

Pharmaceutical Compositions

An embodiment of the present invention includes a composition comprising an admixture of one or more compounds of Formula (I) and/or one or more forms thereof and one or more excipients.

The forms for a compound of Formula (I) include a salt, ester, prodrug or active metabolite of a compound of Formula (I). The form for a compound of Formula (I) further includes a radiolabeled compound of Formula (I), whereby at least one hydrogen atom of the compound of Formula (I) is replaced with a deuterium or tritium atom. Other labeling techniques known to those skilled in the arts may also be used.

The present invention further includes the use of a process for making the composition or medicament comprising mixing one or more of the instant compounds and an optional carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing one or more compounds of Formula (I) or a form, composition or medicament thereof as an active ingredient contains an effective amount of the active ingredient necessary to be therapeutically or prophylactically effective.

The composition or medicament may contain from about 0.001 mg to about 5000 mg (preferably, from about 0.001 to about 500 mg) of active ingredient and may be constituted into any form suitable for the mode of administration selected for a patient in need. A contemplated effective amount may range from about 0.001 mg to about 300 mg/kg of body weight per day. A contemplated effective amount may also range from about 0.003 to about 100 mg/kg of body weight per day. Another contemplated effective amount may range from about 0.1 to about 100 mg/kg of body weight per day. Another contemplated effective amount may also range from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A radiolabeled form of a compound of Formula (I), whereby at least one hydrogen atom of the compound of Formula (I) is replaced with a labeling atom such as a deuterium or tritium atom, may be used as a marker for the kinase receptor. Other labeling techniques known to those skilled in the arts may also be used.

A representative compound of Formula (I) or a form thereof for use in the therapeutic methods and pharmaceutical compositions, medicines or medicaments described herein includes a compound selected from the group consisting of:

| Cpd | Name |
|---|---|
| 1 | ethyl-(5-{2-[3-(4-trifluoromethyl-1H-imidazol-2-yl)-1H-pyrazol-4-yl]-vinyl}-pyridin-3-ylmethyl)-amine |
| 2 | 3-{2-[3-(4-trifluoromethyl-1H-imidazol-2-yl)-1H-pyrazol-4-yl]-vinyl}-pyridine |
| 3 | 2-[4-(2-pyridin-3-yl-vinyl)-1H-pyrazol-3-yl]-1H-imidazole-4-carbonitrile |
| 4 | 4-{2-[3-(4-trifluoromethyl-1H-imidazol-2-yl)-1H-pyrazol-4-yl]-vinyl}-isoquinoline |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations or formulas have the indicated meanings:

| Abbreviation | Meaning |
|---|---|
| BHT | butylated hydroxytoluene |
| Cpd | compound |
| DMF | N,N-dimethyl formamide |
| DMSO | dimethyl sulfoxide |
| EtOAc | ethyl acetate |
| EtOH | ethanol |
| Et$_2$O | diethyl ether |
| HATU | O-(7-azabenzotriazol-1-yl)-N,N,N',N'-tetramethyluronium hexafluorophosphate |
| HOAc | acetic acid |
| MeOH | methanol |
| NaH | sodium hydride |
| NaOAc | sodium acetate |
| min/h/hr/mp | minute/hour/day(s)/melting point |
| Pd(dppf)Cl$_2$•DCM | Dichloro[1,1'-ferrocenylbis(diphenylphosphine)]palladium(II) dichloromethane |
| RT/R.T./rt/r.t. | room temperature |
| SEM-Cl | 2-(trimethyl-silyl)-ethoxymethyl chloride |
| Et$_3$N | triethylamine |
| THF | tetrahydrofuran |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme B

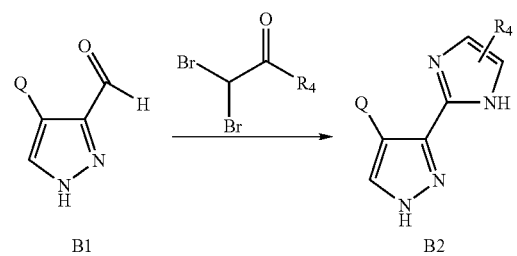

A substituted 1,1-dibromomethylketone is reacted with a substituted pyrazole-3-carbaldehyde Compound B1 (wherein Q represents a halogen leaving group) in a reagent solution (such as a mixture of NaOAc and NH₄OH in a solvent such as aqueous EtOH) to provide a Compound B2.

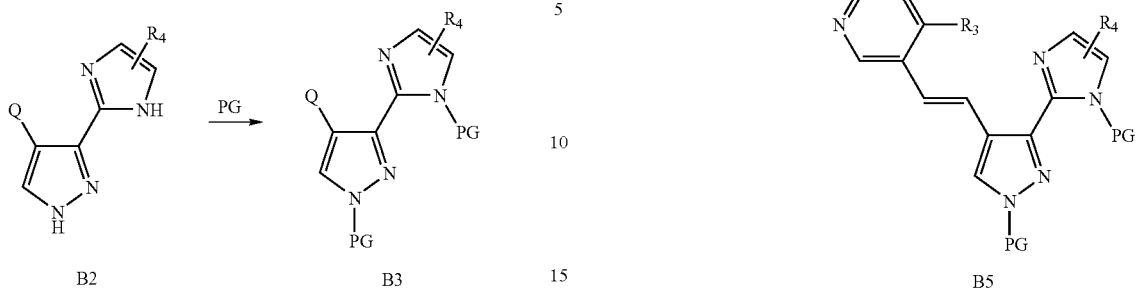

Compound B2 is reacted with a reagent solution (such as a NaH in a solvent such as DMF) then treated with a PG (protecting group) solution (such as SEM-Cl in a solvent such as DMF) to provide a Compound B3.

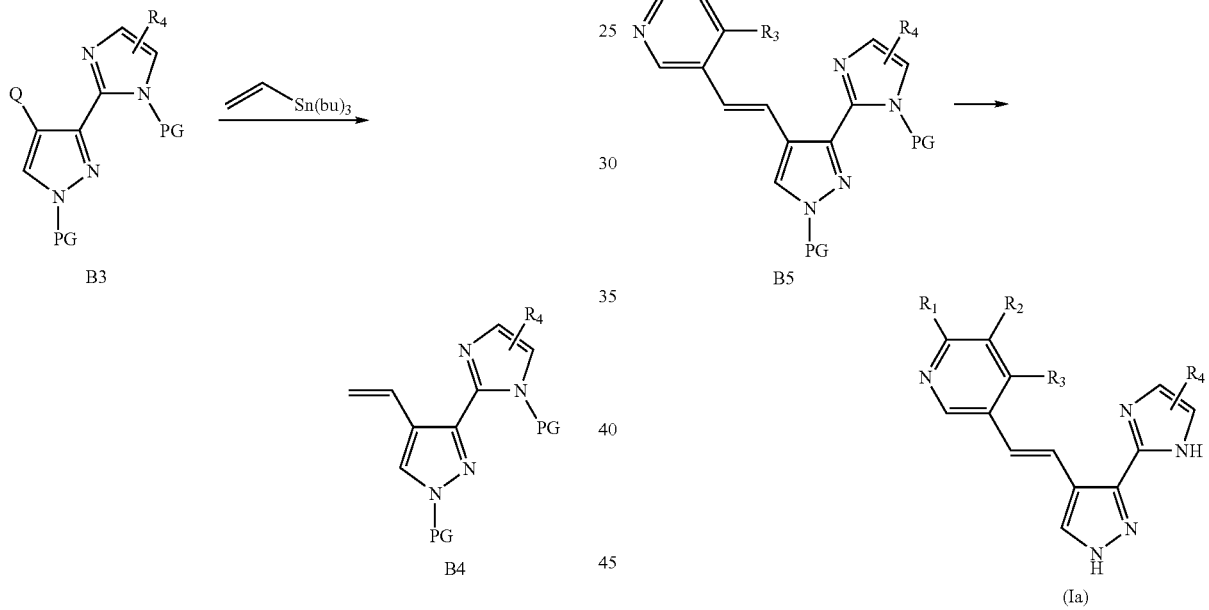

Compound B3 is reacted with tri-butyl-vinyl tin in the presence of a catalyst solution (such as tetrakis(triphenylphosphine) palladium in a solvent such as DMF) to provide a Compound B4.

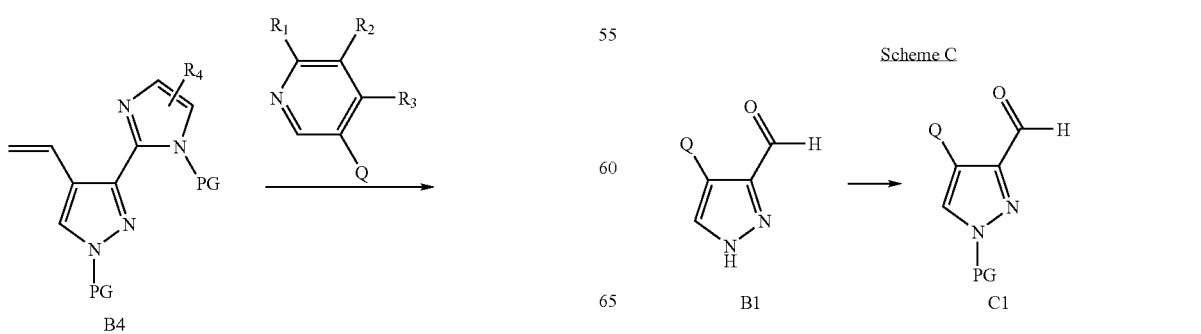

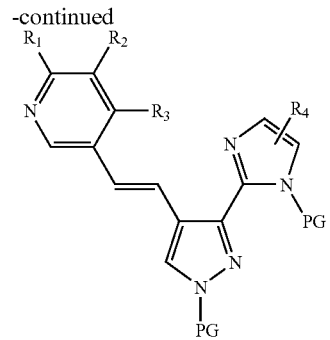

Compound B4 is reacted with a substituted pyridine (wherein Q represents a halogen leaving group) in the presence of a complexed catalyst solution (such as Pd(dppf)Cl₂) and a reagent solution (such as a mixture of Et₃N and BHT in a solvent such as DMF) to provide a Compound B5.

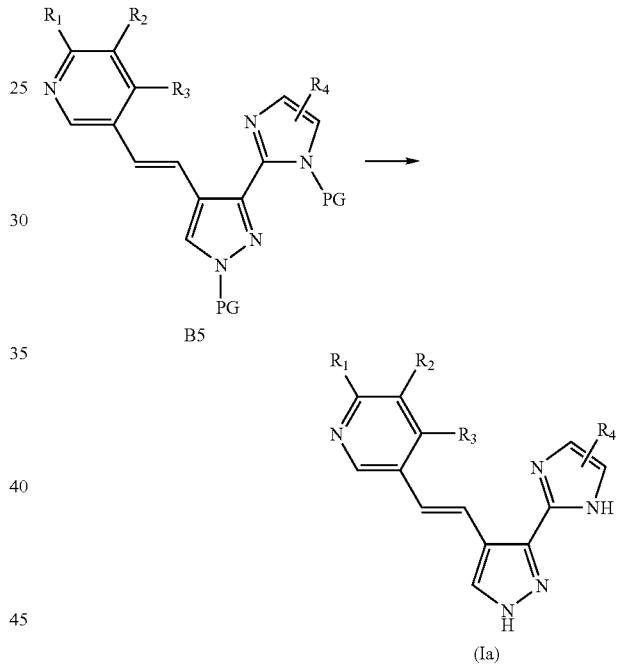

Compound B5 is deprotected using standard techniques to provide a compound of Formula (Ia). The compound of Formula (Ia) may be further substituted using standard functional group transformations known to those skilled in the art to provide additional compounds representative of the present invention.

Scheme C

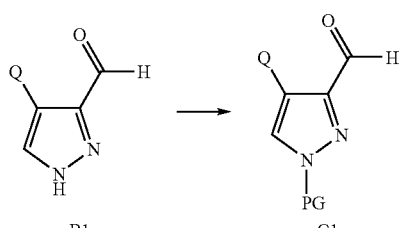

Compound B1 is reacted with a reagent solution (such as a NaH in a solvent such as DMF) then treated with a PG (protecting group) solution (such as SEM-Cl in a solvent such as DMF) to provide a Compound C1.

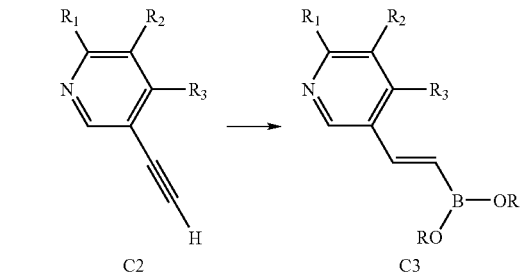

A substituted ethynyl pyridine Compound C2 is reacted with a catalyst solution (such as RuHCl(CO)PPh$_3$) and a reagent solution (such as 4,4,5,5-tetramethyl-[1,3,2]dioxaborolane in a solvent such as toluene) to provide Compound C3.

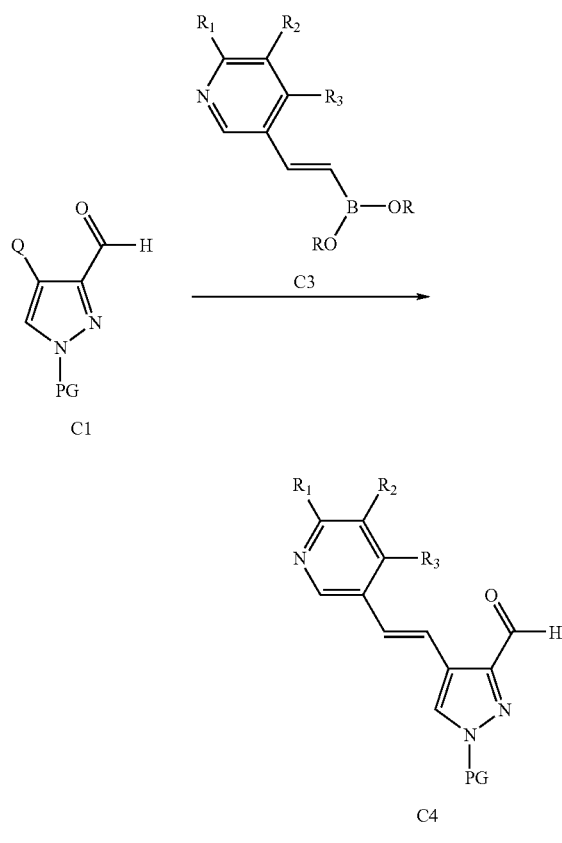

Compound C1 (wherein Q represents a halogen leaving group) is reacted with a Compound C3 in the presence of a complexed catalyst solution (such as Pd(dppf)Cl$_2$.DCM) and a reagent mixture (such as aqueous Na$_2$CO$_3$ in a solvent such as dioxane) to provide a Compound C4.

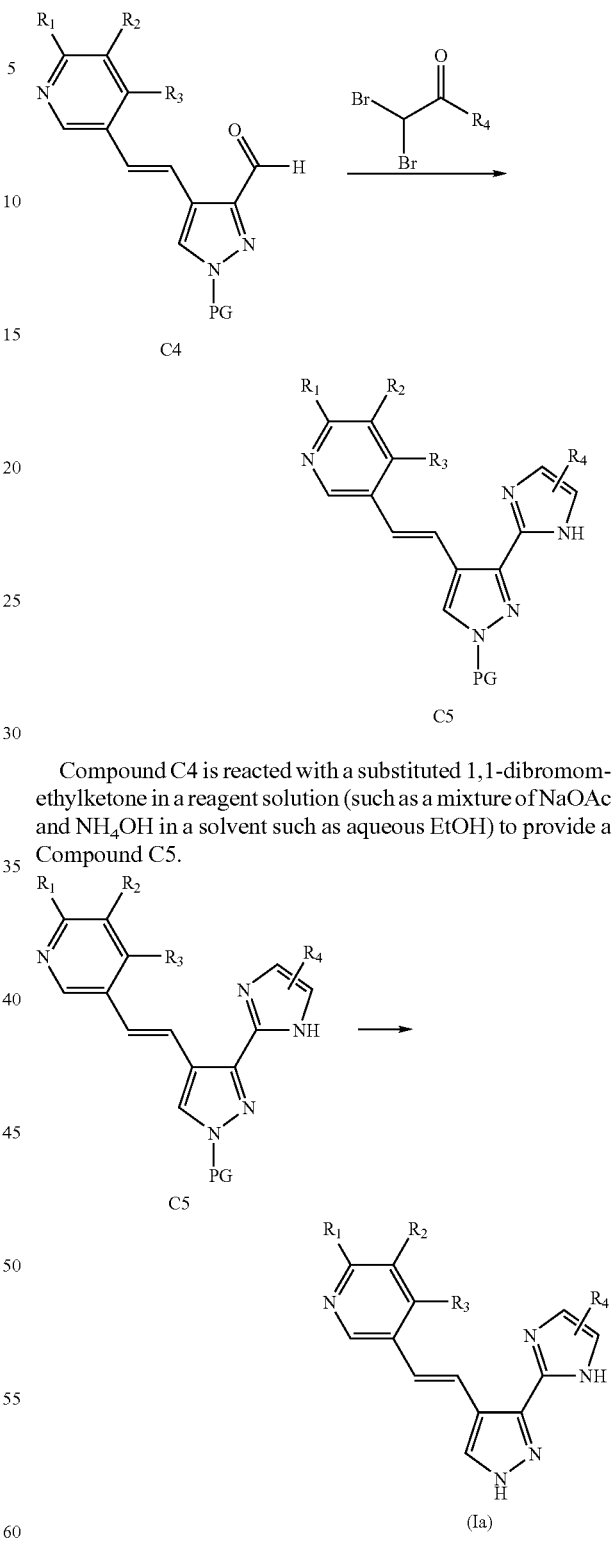

Compound C4 is reacted with a substituted 1,1-dibromomethylketone in a reagent solution (such as a mixture of NaOAc and NH$_4$OH in a solvent such as aqueous EtOH) to provide a Compound C5.

Compound C5 is deprotected using standard techniques to provide a compound of Formula (Ia). The compound of Formula (Ia) may be further substituted using standard functional group transformations known to those skilled in the art to provide additional compounds representative of the present invention.

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

General: $^1$H and $^{13}$C NMR spectra were obtained at 400 MHz and 300 MHz on a Brucker AVANCE300 and AVANCE400 spectrometer. Chemical shifts are reported in ppm downfield from TMS as an internal standard. Magnesium sulfate was employed to dry organic extracts prior to concentration by rotary evaporation. Flash chromatography was done using EM science silica gel 60 (230-400 mesh). Standard solvents from J. T. Baker were used as received. Anhydrous solvents from Aldrich or J. T. Baker and all other commercially available reagents were used without further purification. Silica gel (E. Merck, 230-400 mesh) was used for all flash chromatography. Thin-layer chromatography was performed on precoated plates with silica gel 60 F254 from EM Science. Yields were not optimized. Mass electrospray positive or negative spectra (MS) was performed on Hewlett Packard 1100 series or Agilent 1100 series spectrometer with a Zorbax stablebond C18 narrow bore column, using gradient 0.05% acetic acid in methanol and 0.05% acetic acid in water as mobile phase for MS analysis, and using gradient 0.05% TFA in acetonitrile and 0.05% acetic acid in water as mobile phase for LCMS analysis. HPLC quantitative purity analysis were additionally carried on Agilent 1100 Series LC/MSD equipment on a Agilent 4.6×50 mm Zorbax 3.5 uM column (Elips XDB-phenyl) using gradient 0.05% TFA acetonitrile and 0.05% TFA in water as solvent system and based on the absorption at 254 nM.

Example 1 ethyl-(5-{2-[3-(4-trifluoromethyl-1H-imidazol-2-yl)-1H-pyrazol-4-yl]-vinyl}-pyridin-3-ylmethyl)-amine (Compound 1)

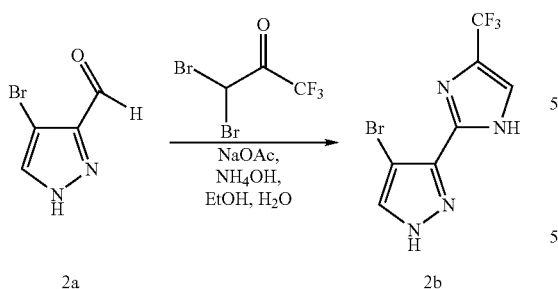

3,3-Dibromo-1,1,1-trifluoro-propan-2-one (12.8 mmol, 3.47 g) was added dropwise to a solution of 3.49 g (25.7 mmol) of NaOAc in 16 mL of water. The resulting white emulsion was refluxed for 30 min to give a clear solution. This solution was added to a suspension of 1.00 g (5.71 mmol) of 4-bromopyrazole-3-carboxaldehyde Compound 2a and in 10 mL of concentrated NH$_4$OH and 60 mL of EtOH. The mixture was stirred at room temperature until HPLC and LC/MS indicated that the reaction was complete. The solvent was evaporated and the residue was partitioned between ethyl acetate and water. The organic layer was separated, dried, and evaporated to give the crude product that was purified by column chromatography to give 4-bromo-3-(4-trifluoromethyl-1H-imidazol-2-yl)-1H-pyrazole Compound 2b that was carried on to the next reaction. MS m/z 281/283 (MH$^+$).

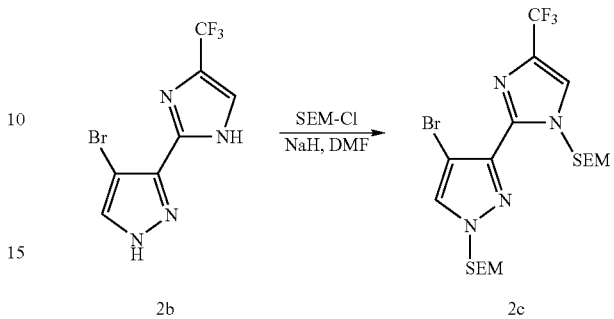

A solution of Compound 2b from the previous reaction in 50 mL of DMF was added gradually to a suspension of 685 mg (17.1 mmol) of NaH (60% oil dispersion) in 10 mL of DMF. After stirring at room temperature for 15 min, a solution of 2.86 g (17.1 mmol) of SEM-Cl in 5 mL of DMF was added. After stirring for 3 h at room temperature, the mixture formed an orange suspension and LC/MS indicated formation of product. The reaction mixture was partitioned between EtOAc and water; the organic layer was washed with water and brine and was concentrated. The resulting crude residue was purified by column chromatography to provide 646 mg (1.19 mmol) of 4-bromo-3-[4-trifluoromethyl-1-(2-trimethylsilanyl-ethoxymethyl)-1H-imidazol-2-yl]-1-(2-trimethylsilanyl-ethoxymethyl)-1H-pyrazole Compound 2c (10% yield for 2 steps); MS m/z 541/543 (MH$^+$).

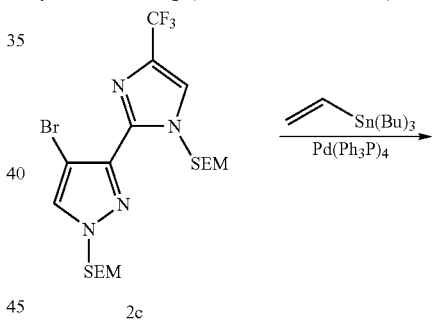

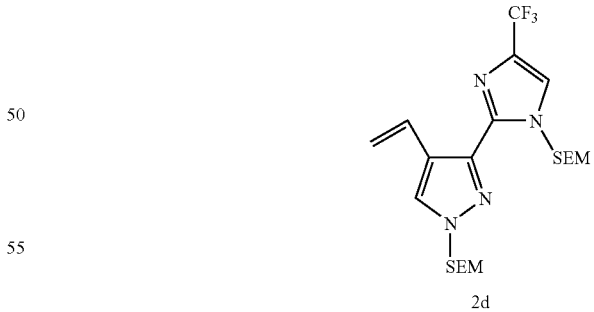

Following the procedure of Example 1, a mixture of 322 mg (0.595 mmol) of Compound 2c and 137 mg (0.119 mmol) of tetrakis(triphenylphosphine) palladium in 40 mL of DMF was treated with a solution of 283 mg (0.892 mmol) of tributyl-vinyl tin in toluene. The mixture was heated at 200° C. in a microwave oven for 20 min. After workup, the crude product was purified by column chromatography to provide 221 mg (0.452 mmol) 3-[4-trifluoromethyl-1-(2-trimethylsilanyl-ethoxymethyl)-1H-imidazol-2-yl]-1-(2-trimethylsilanyl-ethoxymethyl)-4-vinyl-1H-pyrazole Compound 2d (76% yield); MS m/z 489 (MH+).

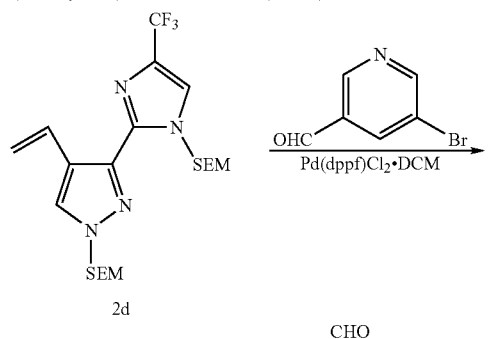

2d

A suspension of 65 mg (0.13 mmol) of Compound 2d, 27 mg (0.15 mmol) of 5-bromo-pyridine-3-carbaldehyde, 22 mg (0.027 mmol) of Pd(dppf)Cl$_2$.DCM, 40 mg (0.40 mmol) of Et$_3$N, and a trace of BHT in DMF was heated at 110° C. overnight. After workup, the crude product was purified by column chromatography to provide 25 mg (0.042 mmol) of 5-{2-[3-[4-trifluoromethyl-1-(2-trimethylsilanyl-ethoxymethyl)-1H-imidazol-2-yl]-1-(2-trimethylsilanyl-ethoxymethyl)-1H-pyrazol-4-yl]-vinyl}-pyridine-3-carbaldehyde Compound 2e (32% yield); MS m/z 594 (MH+)

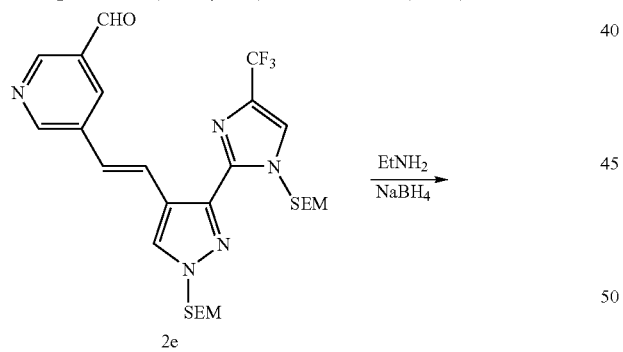

2e 2M ethylamine solution in THF was added to a solution of 25 mg (0.042 mmol) of Compound 2e in MeOH. The mixture was stirred at rt for 2 hrs and NaBH$_4$ powder was added portionwise. The mixture was stirred at rt for 8 hrs. The reaction mixture was worked up to provide 17 mg (0.027 mol) of ethyl-(5-{2-[3-[4-trifluoromethyl-1-(2-trimethylsilanyl-ethoxymethyl)-1H-imidazol-2-yl]-1-(2-trimethylsilanyl-ethoxymethyl)-1H-pyrazol-4-yl]-vinyl}-pyridin-3-ylmethyl)-amine Compound 2f (65% yield); MS m/z 623 (MH+)

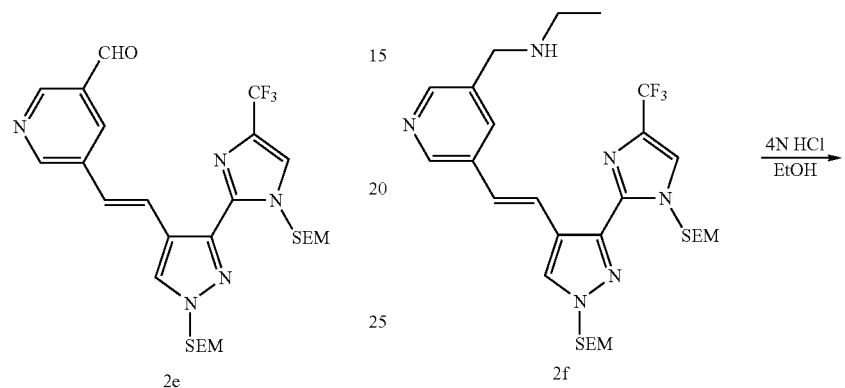

17 mg (0.027 mol) of Compound 2f was dissolved in EtOH and 4N HCl was added. The solution was refluxed for 12 hrs and evaporated to dryness. The residue was purified to provide 10 mg (0.020 mmol) of ethyl-(5-{2-[3-(4-trifluoromethyl-1H-imidazol-2-yl)-1H-pyrazol-4-yl]-vinyl}-pyridin-3-ylmethyl)-amine.4 HCl Compound 1, isolated as a green powder (73% yield). $^1$H NMR (400 MHz, MeOD) 1.17 (t, J=7 Hz, 3H), 3.26 (q, J=7 Hz, 2H) 4.53 (s, 2H), 7.35 (d, J=16.5 Hz, 1H), 7.95 (d, J=16.5 Hz, 1H), 8.03 (s, 1H), 8.42 (s, 1H), 8.92 (s, 1H), 9.09 (s, 1H), 9.14 (s, 1H); MS m/z 363 (MH+)

Using the procedure of Example 1 and the appropriate starting materials, reagents and condition known to those skilled in the art, other compounds representative of the present invention were prepared:

| Cpd | Name | MS |
|---|---|---|
| 4 | 4-{2-[3-(4-trifluoromethyl-1H-imidazol-2-yl)-1H-pyrazol-4-yl]-viny}-isoquinoline | 356 |

Example 2

3-{2-[3-(4-trifluoromethyl-1H-imidazol-2-yl)-1H-pyrazol-4-yl]-vinyl}-pyridine (Compound 2)

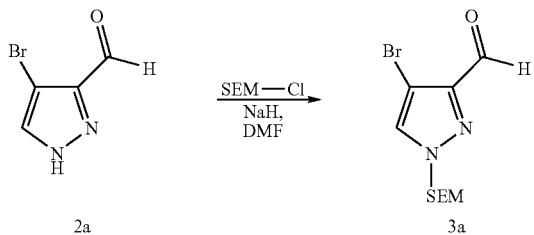

Sodium hydride was added slowly to a clear solution of commercially available 4-bromo-1H-pyrazole-3-carbaldehyde Compound 2a (1 g, 3.56 mmol) in DMF (20 mL). The reaction was stirred at ambient temperature for 20 min; then 2-(trimethylsilyl)ethoxy-methyl chloride (755.7 μL, 4.27 mmol) was added dropwise to the reaction mixture. After the resultant solution was stirred at ambient temperature overnight, water (1 mL) was added to quench the reaction. The reaction mixture was diluted with ethyl acetate and washed with water, saturated sodium bicarbonate, and saturated sodium chloride. The organic solvent was dried over magnesium sulfate. After filtration and evaporation of the solvent in vacuo, the crude product was purified by flash chromatography (10:1 to 4:1 hexane/ethyl acetate) to yield (2-trimethyl-silanyl-ethoxymethyl)-1H-pyrazole-3-carbaldehyde Compound 3a (620 mg, 57% yield) as white solid. $^1$H NMR (300 MHz, CDCl$_3$) δ 9.97 (s, 1H), 7.64 (s, 1H), 5.81 (s, 2H), 3.62 (t, 2H), 0.93 (t, 2H), 0 (s, 9H); MS (ESI) m/z: 306.7 (M+H$^+$), 328.7 (M+Na$^+$).

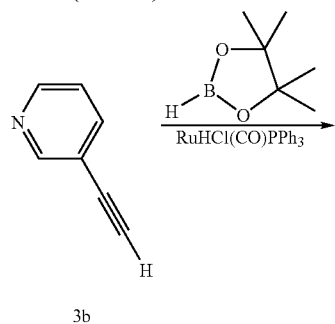

Commercially available 3-ethynyl-pyridine 3b (1.03 g, 10 mmol) and 4,4,5,5-tetramethyl-[1,3,2]dioxaborolane (7.26 mL, 50 mmole) in toluene (40 mL) were combined with carbonylchlorohydridotris(triphenylphosphine) ruthenium (II), RuHCl(CO)(PPh$_3$) (476 mg, 0.50 mmol) at ambient temperature and the reaction mixture was heated at 50° C. in an oil-bath for 16 h. The toluene was evaporated and the crude compound was diluted with ethyl acetate and washed with saturated sodium bicarbonate solution, saturated sodium chloride solution, and water. The organic extracts were dried over MgSO$_4$, filtered, and evaporated in vacuo. The crude product was eluted with a gradient of 10:1 to 2:1 hexane/ethyl acetate by flash chromatography to yield 3-[2-(4,4,5,5-tetramethyl-[1,3,2]dioxaborolan-2-yl)-vinyl]-pyridine Compound 3c (2.2 g, 95% yield) as a yellow syrup. $^1$H NMR (300 MHz, CDCl$_3$) δ 8.75 (d, 1H), 8.54 (dd, 1H), 7.83 (dt, 1H), 7.39 (d, 1H), 7.31 (dd, 1H), 6.27 (d, 1H), 1.34 (s, 12H); MS (ESI) m/z: 232.14 (M+H$^+$).

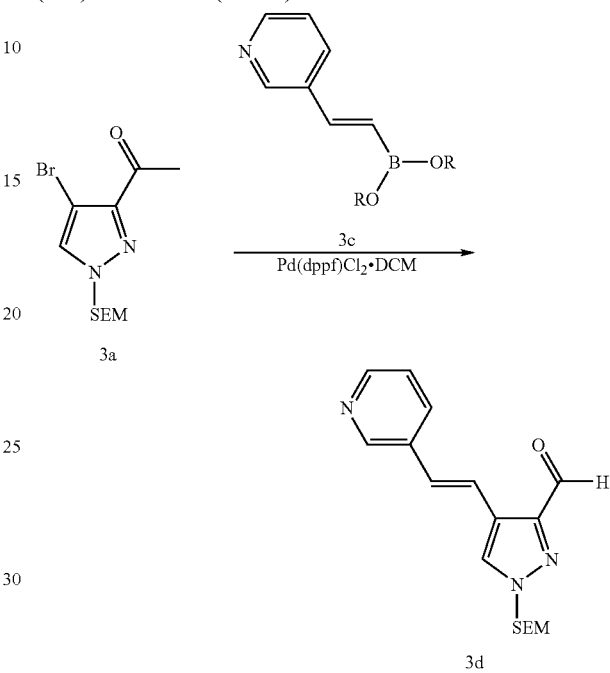

After the solution of 4-bromo-1-(2-trimethylsilanyl-ethoxymethyl)-1H-pyrazole-3-carbaldehyde Compound 3a (570 mg, 1.87 mmol) and 3-[2-(4,4,5,5-tetramethyl-[1,3,2]dioxaborolan-2-yl)-vinyl]-pyridine Compound 3c (863 mg, 3.74 mmol) in dioxane (35 mL) was degassed by evacuating and purging with nitrogen. [1,1'-Bis(diphenylphosphino)-ferrocene]dichloropalladium(II) complex (Pd(dppf)$_2$Cl$_2$) (273 mg, 0.374 mmol) and sodium carbonate in water (3.74 mL, 2M) were added to the reaction mixture. The resultant suspension was purged again with nitrogen and heated at 120° C. for 30 min in a microwave reactor. After the solvent was removed in vacuo, the residue was dissolved in methanol and loaded to silica gel directly. The crude compound was eluted with a gradient of 4:1 to 2:1 hexane/ethyl acetate by flush chromatography to yield 4-(2-pyridin-3-yl-vinyl)-1-(2-trimethylsilanyl-ethoxymethyl)-1H-pyrazole-3-carbaldehyde Compound 3d (385.6 mg, 0.624 mmol, 72% yield) as a white solid. $^1$H NMR (300 MHz, CDCl$_3$) δ 10.26 (s, 1H), 8.75 (s, 1H), 8.55 (d, 1H), 7.91 (m, 3H), 7.54 (d, 1H), 7.50 (t, 2H), 7.34 (dd, 2H), 7.11 (d, 1H), 5.82 (s, 2H), 3.62 (t, 2H), 0.94 (t, 2H), 0 (s, 9H); MS (ESI) m/z: 330.1 (M+H$^+$).

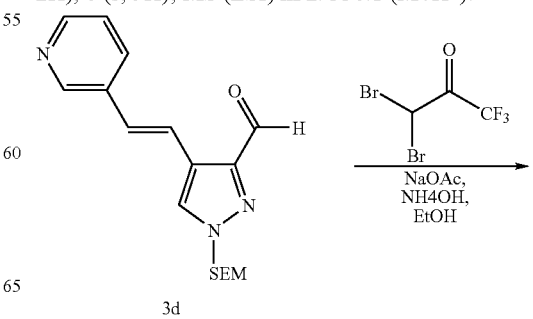

-continued

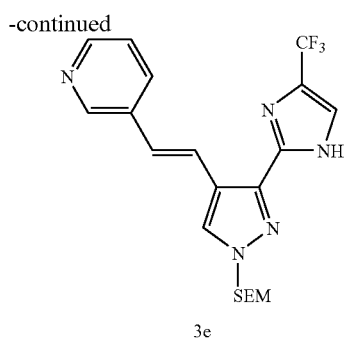

3e

A clear solution of sodium acetate (599 mg, 7.30 mmol) and 3,3-dibromo-1,1,1-trifluoro-propan-2-one (432 μL, 3.647 mmol) in 15 mL water was heated at 100° C. for 50 min. Upon cooling a solution of Compound 3d (400 mg, 1.22 mmol) in ethanol (25 mL) and concentrated ammonium hydroxide (4.65 mL) was added to the reaction mixture. The reaction mixture was stirred at ambient temperature for 24 h. The solvent was removed in vacuo and the residue was partitioned between ethyl acetate and saturated sodium bicarbonate. The organic extracts were washed with saturated sodium chloride, water and dried over magnesium sulfate. After concentration, the crude product was purified by silica gel chromatography (eluting with a gradient of 10:1 to 8:1 hexane/ethyl acetate) to provide 3-{2-[3-(4-trifluoromethyl-1H-imidazol-2-yl)-1-(2-trimethylsilanyl-ethoxymethyl)-1H-pyrazol-4-yl]-vinyl}-pyridine Compound 3e as a yellow solid 3e (292 mg, 0.67 mmol, 55% yield). $^1$H NMR (300 MHz, CDCl$_3$) δ 11.52 (s, 1H), 8.61 (s, 1H), 8.40 (d, 1H), 7.90 (s, 1H), 7.82 (d, 1H), 7.70 (d, 1H), 7.65 (s, 1H), 7.52 (s, 1H), 7.28 (m, 1H), 6.95 (d, 1H), 5.61 (s, 2H), 3.74 (t, 2H), 0.98 (t, 2H), 0 (s, 9H); MS (ESI) m/z: 436.2 (M+H$^+$).

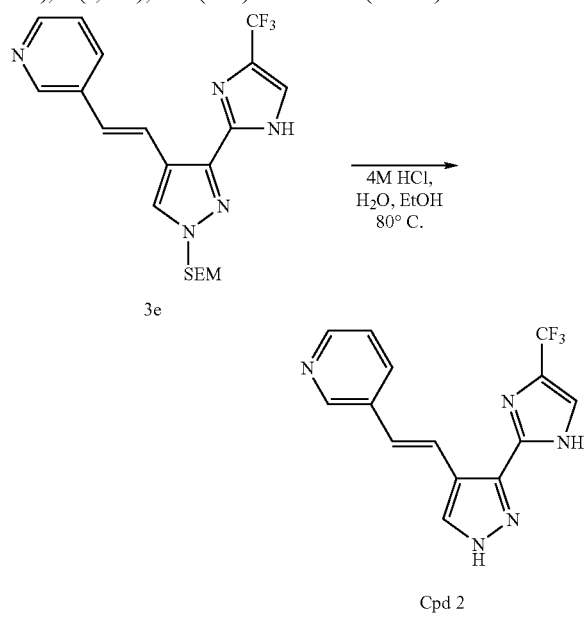

Compound 3e (160 mg, 0.368 mmol) in ethanol (30 mL) was treated with 4M aqueous hydrochloric acid (15 mL). The reaction was stirred at 80° C. for 16 h and the solvent was removed in vacuo. The residue was dissolved in methanol and neutralized with several drops of 2M aqueous sodium hydroxide to pH~7. The solvent was evaporated and the crude compound was diluted with ethyl acetate and washed with water. The organic extracts were dried over magnesium sulfate, filtered, and evaporated in vacuo. The crude product was purified by flash chromatography with 10% methanol/dichloromethane to provide 3-{2-[3-(4-trifluoromethyl-1H-imidazol-2-yl)-1H-pyrazol-4-yl]-vinyl}-pyridine Compound 2 as a white solid (112 mg, 100%). $^1$H NMR (300 MHz, CDCl$_3$) δ 7.11 (d, J=16.5 Hz, 1H), 7.42 (dd, J=5, 7.8 Hz, 1H), 7.62 (s, 1H), 7.82 (broad d, J=16 Hz, 1H), 8.02 (d, J=8.3 Hz, 1H), 8.16 (s, 1H), 8.36 (d, J=3.6 Hz, 1H), 8.62 (s, 1H); MS (ESI) m/z: 306.3 (M+H$^+$).

Example 4

2-[4-(2-pyridin-3-yl-vinyl)-1H-pyrazol-3-yl]-1H-imidazole-4-carbonitrile (Compound 3)

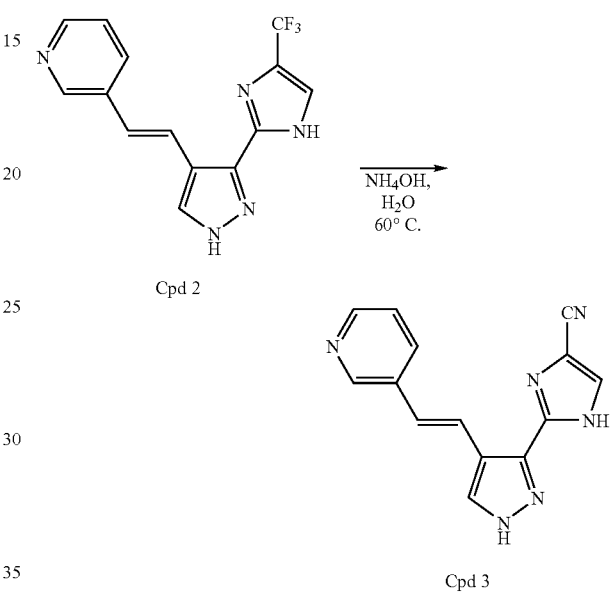

A mixture of 3-{2-[3-(4-trifluoromethyl-1H-imidazol-2-yl)-1H-pyrazol-4-yl]-vinyl}-pyridine Compound 2 (50 mg, 0.164 mmole) and 5% aqueous ammonium hydroxide (20 mL) was stirred at 60° C. for 3 h until all of the starting material disappeared. After the solvent was removed in vacuo, the residue was dissolved in methanol and neutralized with several drops of 2M aqueous HCl to pH~7. The solvent was evaporated and the crude compound was diluted with ethyl acetate and washed with water. The organic extracts were dried over MgSO$_4$, filtered, and evaporated in vacuo. The product was purified by flash chromatography with 10% methanol/dichloromethane to give 2-[4-(2-pyridin-3-yl-vinyl)-1H-pyrazol-3-yl]-1H-imidazole-4-carbonitrile Compound 3 as a white solid (21.5 mg, 50%). $^1$H NMR (300 MHz, MeOD) δ 7.10 (d, J=16.5 Hz, 1H), 7.44 (dd, J=5, 7.8 Hz, 1H), 7.82 (d, J=14 Hz, 1H), 7.92 (s, 1H), 8.09 (d, J=7.7 Hz 1H), 8.18 (s, 1H), 8.37 (dd, J=1.5, 5 Hz, 1H), 8.63 (d, J=2 Hz, 1H); MS (ESI) m/z: 263.7 (M+H$^+$).

Biological Examples

The ability of the compounds to treat or ameliorate protein kinase mediated disorders was determined using the following procedures.

Example 1

CDK-1, VEGFR2, HER2, and Aurora-A Screening Assays

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated histone-H1 peptide substrate and 0.2 μCuries per well $^{33P}$-γ-ATP (2000-3000

Ci/mmol). 70 μL of the kinase reaction mixture was dispensed into the well of a streptavidin coated FlashPlate™ (Cat. # SMP103, NEN, Boston, Mass.).

Test compound stock in 100% DMSO (1 μL) was added to the wells resulting in a final concentration of 1% DMSO in the reaction with a 100 μL final reaction volume. Each enzyme was diluted in 50 mM Tris-HCl pH=8.0, 0.1% BSA and 30 μL was added to each well to initiate the reaction. The reaction was incubated for one hour at 30° C. At the end of the 1 hr incubation, the reaction was terminated by aspirating the mixture from the plate and washing the wells twice with PBS containing 100 mM EDTA. The biotinylated peptide substrate became immobilized on the Flashplate™ and the incorporation of $^{33}P$-γ-ATP was measured by reading the plate on a scintillation counter. Inhibition of the enzymatic activity was measured by observing a reduced amount of $^{33}P$-γ-ATP incorporated into the immobilized peptide.

The CDK1 enzyme was isolated from insect cells expressing both the human CDK1 catalytic subunit (Accession number NM_001786) and its positive regulatory subunit cyclin B (New England Biolabs, Beverly, Mass.; Cat. #6020). The assay used 30 ng of the N-terminal biotinylated peptide biotin-KTPKKAKKPKTPKKAKKL-amide (Cyclin dependent kinase 1) per well.

The VEGF-R2 enzyme is a fusion protein containing a polyhistidine tag at the N terminus followed by amino acids 786 to 1343 of the rat VEGF-R2 kinase domain (Accession number U93306). The assay used 150 ng of the N-terminal biotinylated peptide biotin-AEPDYGALYEGRNPG-FYVEANP-amide (VEGF-R2) per well.

The HER2 construct consisted of a fusion of GST (Glutathione-S-Transferase), HIS6 Thrombin and the nucleotides encoding amino acids 679 to 1255 of HER-2 (Accession number M11730) (Proqinase, Freiburg, Germany). The assay used 200 ng of the N-terminal biotinylated peptide biotin-poly(GT) 4:1 (HER2) per well.

Aurora-A is a fusion protein containing a polyhistidine tag at the N terminus followed by the full length protein encoding the murine Aurora-A (Accession number GB BC014711) expressed and purified from sf9 insect cells. The assay used 400 ng of the N-terminal biotinylated peptide biotin-GRT-GRRNSI-amide (Aurora-A) per well.

A maximum and minimum signal for the assay was determined on each plate. The percent inhibition of a test compound was calculated according to the formula:

$$\left[\frac{(\text{max signal} - \text{test compound})}{(\text{max signal} - \text{min signal})}\right](100) = \% \text{ inhibition}$$

For a series of test concentrations, the $IC_{50}$ was derived by graphing percent inhibition against the log of the concentrations tested for a given compound with results shown in Table 1.

TABLE 1

| | $IC_{50}$ (average) (μM) | | | |
|---|---|---|---|---|
| Cpd | CDK1 | HER2 | VEGFR2 | Aurora-A |
| 1 | 0.01805 | >100 | ~10 | >10 |
| 2 | 0.4834 | >100 | 29.39 | 0.1168 |
| 3 | 0.7036 | >100 | >10 | >10 |
| 4 | 0.1131 | 32.73 | 3.063 | 0.297 |

Example 2

Cell Proliferation Inhibition Assay

The ability of a test compound to inhibit unregulated cell proliferation may be determined by measuring incorporation of $^{14}C$-labelled thymidine into newly synthesized DNA within cell lines derived from carcinomas originating from several tissues. Accordingly, the anti-proliferative effect of a compound on cells with a variety of phenotypes may be determined.

Carcinoma cell lines include those such as HeLa cervical adenocarcinoma (American Type Culture Collection (ATCC), Virginia, Cat. #CCL-2), A375 malignant melanoma (ATCC CRL-1619), and HCT-116 colon carcinoma (CCL-247).

The carcinoma cells are trypsinized and counted. The cells (3000-8000 count) are added to each well of a 96-well CytoStar tissue culture treated scintillating microplate (Amersham #RPNQ0160) in complete medium (100 μL) and the plate is then incubated in complete medium for 24 hrs at 37° C. in an inert atmosphere containing 5% $CO_2$. Test compound (1 μL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}C$-thymidine (56 mC/mmol) (NEN #NEC568 or Amersham #CFA532) and complete medium (20 uL to provide 0.2 μCi/well) is then added to each well and the plate is incubated for a third 24 hr period at 37° C. in an atmosphere containing 5% $CO_2$. The plate contents are then discarded, the plate is washed twice with PBS (200 μL) and then PBS (200 μL) is added to each well. The plate is sealed and the degree of methyl $^{14}C$-thymidine incorporation is quantified on a Packard Top Count.

A maximum and minimum signal for the assay was determined on each plate. The percent inhibition of a test compound was calculated according to the formula:

$$\left[\frac{(\text{max signal} - \text{test compound})}{(\text{max signal} - \text{min signal})}\right](100) = \% \text{ inhibition}$$

For a series of test concentrations, the $IC_{50}$ was derived by graphing percent inhibition against the log of the concentrations tested for a given compound with results shown in Table 3.

TABLE 2

| | $IC_{50}$ (average) (μM) | | |
|---|---|---|---|
| Cpd | A375 | HCT-116 | HeLa |
| 1 | 7.436 | 1.746 | 3.175 |
| 2 | 46.54 | 23.82 | >10 |
| 3 | >10 | 70.7 | >10 |
| 4 | 5.589 | 2.915 | 3.582 |

Example 3

In Vivo Models—Inhibition of Tumor Growth

The ability of a test compound to inhibit unregulated growth of human tumor cells in vivo may be evaluated by implanting human tumor cells into the hindflank of athymic mice, administering a test compound and then quantifying any change in tumor size.

Human epidermoid A431 carcinoma cells ($10^6$ count) are implanted subcutaneously into the hindflank of female athymic mice (Charles River) and allowed to grow for 6-10 days. After a measurable tumor is established (as determined by baseline caliper measurement), the animal is administered an oral dose of the test compound (in 10% solutol) daily for a period of 30 days. Tumor size is measured every five days and the degree of inhibition is determined by comparing drug-treated animals to vehicle-treated animals.

Variations of this method are intended to include intraperitoneal injection or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I):

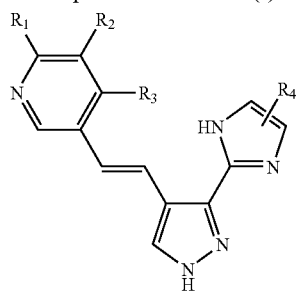

or a salt thereof, wherein $R_1$ is hydrogen, hydroxy, halo, $C_{1-6}$alkyl, $C_{1-6}$alkoxy, amino or $C_{1-6}$alkyl-amino;

$R_2$ is hydrogen, hydroxy, $C_{1-6}$alkyl, $C_{1-6}$alkoxy, amino, $C_{1-6}$alkyl-amino, amino-$C_{1-6}$alkyl, $C_{1-6}$alkyl-amino-$C_{1-6}$alkyl, $C_{1-6}$alkoxy-carbonyl, $C_{1-6}$alkyl-amino-carbonyl or cyano;

$R_3$ is hydrogen or $C_{1-6}$alkyl;

alternatively, $R_2$ and $R_3$ are taken together to form —CH=CH—CH=CH—; and $R_4$ is hydrogen, trihalo-$C_{1-6}$alkyl, trihalo-$C_{1-6}$alkoxy or cyano.

2. The compound of claim 1 wherein R1 is hydrogen, halo or amino; or a salt thereof.

3. The compound of claim 1 wherein $R_2$ is hydrogen, $C_{1-6}$alkoxy, $C_{1-6}$ alkyl-amino-$C_{1-6}$alkyl, $C_{1-6}$alkoxy-carbonyl, $C_{1-6}$alkyl-amino-carbonyl or cyano; or a salt thereof.

4. The compound of claim 1 wherein the compound is selected from the group consisting of

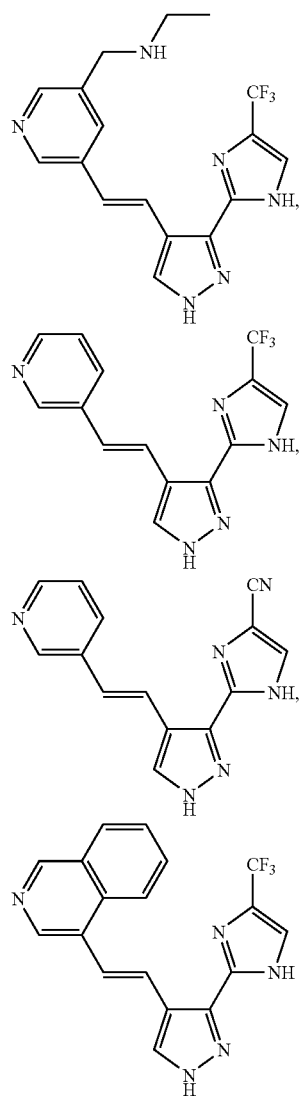

and salt thereof.

5. The compound of claim 1 wherein the compound or a salt thereof is an inhibitor of ATP-protein kinase interactions.

6. The compound of claim 1 wherein the compound is in an isolated salt.

* * * * *